(12) United States Patent
Tanassi et al.

(10) Patent No.: US 8,857,987 B2
(45) Date of Patent: Oct. 14, 2014

(54) OPHTHALMIC APPARATUS

(75) Inventors: Cesare Tanassi, Susegana (IT); Enzo Maria Vingolo, Rome (IT); Raffaella Bisson, Padua (IT); Mauro Campigotto, Camposampiero (IT)

(73) Assignee: Nidek Co., Ltd., Gamagori-shi (JP)

( * ) Notice: Subject to any disclaimer, the term of this patent is extended or adjusted under 35 U.S.C. 154(b) by 178 days.

(21) Appl. No.: 13/150,917

(22) Filed: Jun. 1, 2011

(65) Prior Publication Data

US 2011/0304821 A1 Dec. 15, 2011

(30) Foreign Application Priority Data

Jun. 10, 2010 (JP) ................................. 2010-133382

(51) Int. Cl.
*A61B 3/14* (2006.01)
*A61B 3/10* (2006.01)
*A61B 3/12* (2006.01)
*A61B 3/00* (2006.01)

(52) U.S. Cl.
CPC ................. *A61B 3/12* (2013.01); *A61B 3/0091* (2013.01)
USPC .......................................... 351/206; 351/211

(58) Field of Classification Search
USPC ......... 351/200, 206, 205, 222, 221, 208–211, 351/216, 243–245
See application file for complete search history.

(56) References Cited

U.S. PATENT DOCUMENTS

| | | | |
|---|---|---|---|
| 6,158,863 A * | 12/2000 | Afran ............................ | 351/202 |
| 6,636,696 B2 * | 10/2003 | Saito ............................. | 396/18 |
| 6,705,726 B2 | 3/2004 | Tanassi et al. | |
| 7,377,646 B2 | 5/2008 | Suzuki | |
| 2002/0102099 A1 | 8/2002 | Saito | |
| 2003/0234908 A1 * | 12/2003 | Kushida ....................... | 351/206 |

FOREIGN PATENT DOCUMENTS

| | | |
|---|---|---|
| EP | 1 452 126 A1 | 9/2004 |
| EP | 1 535 566 A1 | 6/2005 |
| EP | 1 935 329 A1 | 6/2008 |
| EP | 1 972 266 A1 | 9/2008 |
| EP | 2 138 826 A1 | 12/2009 |
| JP | A-2003-235800 | 8/2003 |
| JP | A-2005-342107 | 12/2005 |
| JP | A-2010-233978 | 10/2010 |
| WO | WO 2008/062527 A1 | 5/2008 |

OTHER PUBLICATIONS

Sep. 28, 2011 Search Report issued in European Application No. 11169189.5.

* cited by examiner

*Primary Examiner* — Thomas K Pham
*Assistant Examiner* — Brandi Thomas
(74) *Attorney, Agent, or Firm* — Oliff PLC (57) ABSTRACT

An ophthalmic apparatus comprising: a fundus observation optical system; a designating part for designating an area of the fundus other than a macular area from a fundus image displayed on a monitor to make alignment of the fundus area of the fundus image displayed on the monitor with the fixation target displayed on a LCD display; a judging part for detecting an approaching state of the fixation target projected on the fundus and the designated fundus area based on positional information of the fundus area designated by the designating part on the monitor after movement and positional information of the fixation target displayed on the LCD display, and judging based on a detection result, whether or not the designated fundus area and the fixation target projected on the fundus are coincident in a predetermined allowable range; and a display control part for changing the display state of the fixation target based on a judgment result of the judging part.

8 Claims, 5 Drawing Sheets

OPHTHALMIC APPARATUS

CROSS-REFERENCE TO RELATED APPLICATIONS

This application is based upon and claims the benefit of priority from the prior Japanese Patent Application No. 2010-133382, filed on Jun. 10, 2010, the entire contents of which are incorporated herein by reference.

TECHNICAL FIELD

The present invention relates to an ophthalmic apparatus equipped with a rehabilitation function for use in visual function training for examinees with a disease of a macular area to see objects by utilizing a remaining retinal function.

BACKGROUND ART

Heretofore, there is known a perimeter for diagnosing an abnormal visual field such as visual field defects. This perimeter presents targets for a visual field examination in a position excepting a place on which a fixation target appears while an examinee gazes at the fixation target. Then, brightness difference thresholds of the target are detected over a wide range of the visual field based on responses from the examinee. There is also known a fundus perimeter including a fundus observation optical system for observing and photographing a fundus. This perimeter can be used both as a fundus photographing apparatus and for visual field examination (WO2008/062527).

In the case where a disease is found in a macular area which is normally most sensitive to vision in a visual field examination using a perimeter, i.e., in the case where the macular area is detected as not functioning properly, an examinee has to see objects by using another region of a retina with a remaining visual function. However, if an examinee who has seen objects heretofore mainly through a macular area is expected to see objects by positively using another region of the fundus other than the macular area, he/she needs to undergo some training.

SUMMARY OF INVENTION

Technical Problem

The present invention has a purpose to provide an ophthalmic apparatus provided with a rehabilitation function for allowing an examinee to undergo visual function training to see objects by using his/her visual function.

Solution to Problem

To achieve the above purpose, the invention provides the following configurations.

An ophthalmic apparatus comprises: a fundus observation optical system including an image pickup element to observe a fundus of an examinee's eye; a target presenting optical system for projecting a fixation target onto the fundus, the target presenting optical system including an LCD display for displaying a predetermined fixation target; a monitor for displaying an image of the fundus picked up by the image pickup element; a designating part for designating an area of the fundus other than a macular area from the fundus image displayed on the monitor to make alignment of the fundus area of the fundus image displayed on the monitor with the fixation target displayed on the LCD display; a judging part for detecting an approaching state of the fixation target projected on the fundus and the designated fundus area based on positional information of the fundus area designated by the designating part on the monitor after movement and positional information of the fixation target displayed on the LCD display, and judging based on a detection result, whether or not the designated fundus area and the fixation target projected on the fundus are coincident in a predetermined allowable range; and a display control part for changing the display state of the fixation target based on a judgment result of the judging part.

DESCRIPTION OF EMBODIMENTS

A detailed description of a preferred embodiment of the present invention will now be given referring to the accompanying drawings. This embodiment exemplifies a fundus perimeter including both the function of measuring a visual field of an examinee's eye (a distribution of visual sensitivity) and the function of observing and photographing a fundus. The following explanation is given to an example of training (rehabilitation) using a fundus perimeter for an examinee with disease of a macular area (a central fovea) to see objects by utilizing a remaining visual field of a retina.

Figure 1:
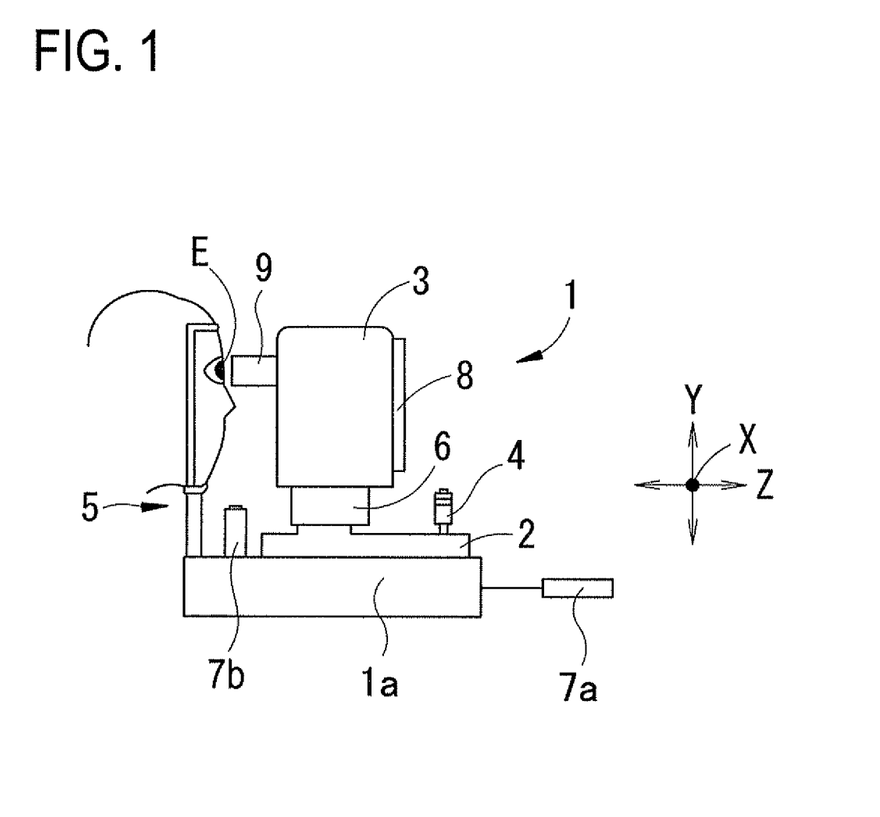
FIG. 1 is an external configuration view of a fundus perimeter.

FIG. 1 is an external view of the fundus perimeter in this embodiment. The fundus perimeter 1 includes a base 1a, a movable table 2 placed movably right and left (an X direction) and back and forth (a working distance; a Z direction) relative to the base 1a, a photographing part (a main unit) 3 placed movably right and left (the X direction), up and down (a Y direction), and back and forth (the Z direction), and a head supporting unit 5 fixedly placed on the base 1a to support the head of an examinee. The photographing part 3 contains optical systems mentioned later.

The photographing part 3 is moved in XYZ directions (in three dimensional directions) relative to an eye E of the examinee by an electric-powered XYZ driving part 6 provided in the movable table 2. The fundus perimeter 1 includes a joystick 4 for relatively moving the photographing part 3 with respect to the eye E. When the joystick 4 is tilted, a sliding mechanism slides the movable table 2 in the X and Z directions on the base 1a. When a rotary knob (not shown) of the joystick 4 is rotated, the XYZ driving part 6 is activated to move the photographing part 3 in the Y direction.

On an examiner side of the photographing part 3, a monitor 8 is provided. This monitor 8 selectively displays thereon a fundus observation screen, an anterior segment observation screen, a visual field examination screen, a rehabilitation screen, and others. An examiner observes motions and others of the examinee's eye E on the monitor 8. On the examiner side of the photographing part 3, a control unit 7a is also provided. This control unit 7a is used as an input device for setting check conditions in various examinations as well as a designating device for designating an area of the fundus with a visual function (a preferred retinal locus (PRL) which is a substitute portion of a macular area) in a visual function training (rehabilitation) mentioned later. It is to be noted that the control unit 7a may be any known input device such as a mouse, a keyboard, and a touch panel (attached to the monitor 8). On an examinee side of the photographing part 3, there are provided a photographing window 9 through which the examinee peers and a response button 7b whereby the examinee inputs a response signal during the visual field examination.

Figure 2:
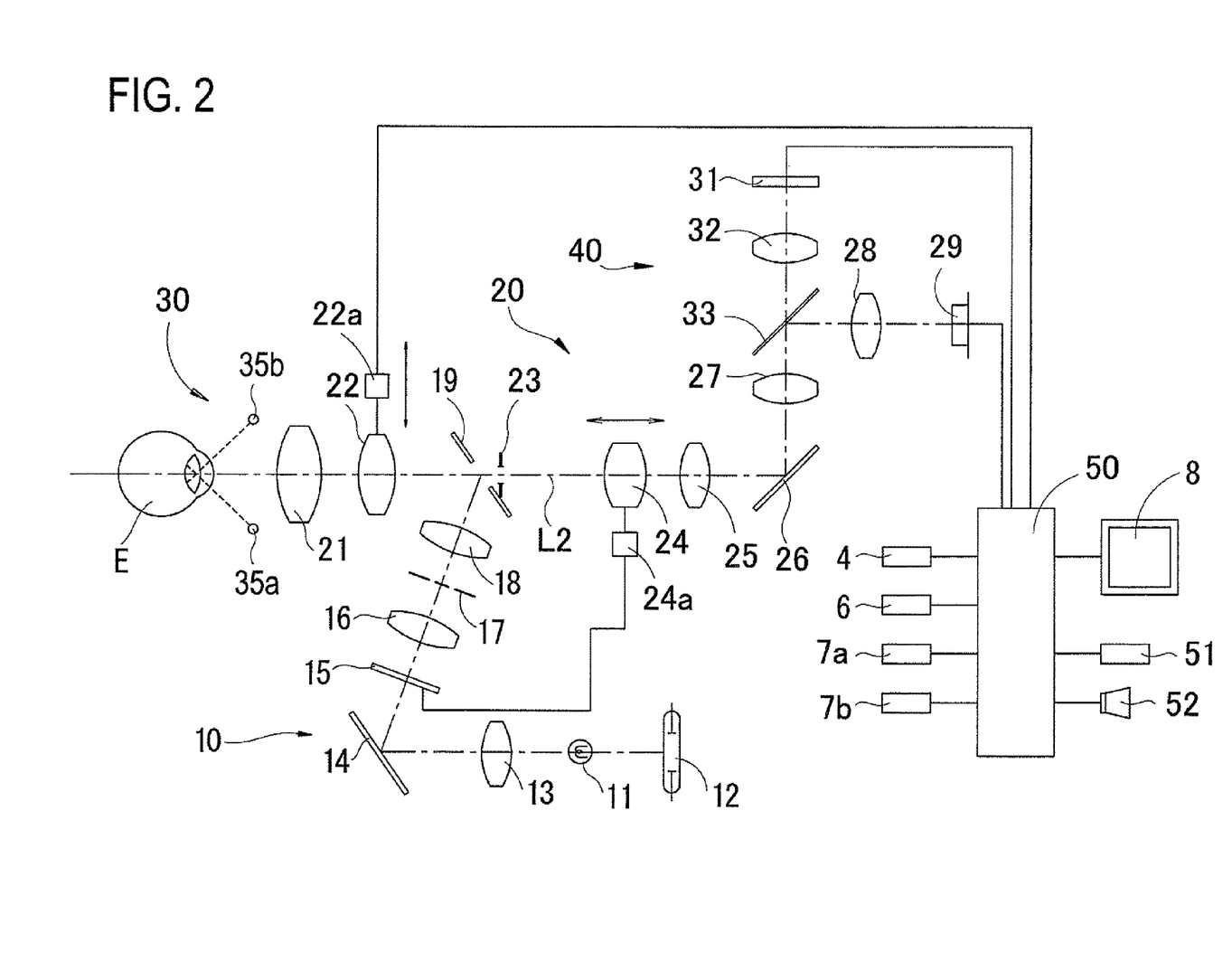
FIG. 2 is a schematic configuration view of optical systems and a control system which are contained in a photographing part.

FIG. 2 is a schematic configuration view of optical systems and a control system. A fundus illumination optical system 10 for illuminating the fundus of the examinee's eye E includes a light source 11 that emits infrared light, a light source 12 that emits flash light of a visible range during photographing of the fundus, a collimator lens 13, a total reflection mirror 14, a focus chart 15, a condenser lens 16, a ring slit 17 having a ring-shaped aperture, a relay lens 18, a perforated mirror 19, and an objective lens 21.

The focus chart 15 is made of a filter that allows visible light and infrared light to pass therethrough and is formed thereon with a ring target of a predetermined size. The ring target is formed by a coating having the property of allowing passage of visible light and disallowing passage of infrared light. Therefore, a part of infrared light is blocked by the ring target during observation of the fundus in which the infrared light source lights up, so that the ring target with a dark luminance is projected on the fundus. On the other hand, during photographing of the fundus in which the visible light source 12 lights up, the visible light passes through the entire focus chart 15 including the ring target, so that the fundus is entirely illuminated.

It is preferable that the thickness of the ring target of the focus chart 15 is sufficiently larger than the thickness of blood vessels for the purpose of distinction from the blood vessels and others. The focus chart 15 can be moved along an optical axis L2 together with a focusing lens 24 mentioned later by a driving means 24a. When the focusing lens 24 is moved along the optical axis L2 so that a ring width of the ring target of the focus chart 15 is narrowest, the fundus comes into focus.

Infrared light emitted from the light source 11 passes through the collimator lens 13 to illuminate the focus chart 15 from behind. The light passing through the focus chart 15 passes through the components, from the relay lens 16 to the objective lens 21, to form an image on the fundus. A ring image is thus projected on the fundus. On the other hand, the infrared light passing through the ring slit 17 passes through the relay lens 18 is reflected by the perforated mirror 19, passes through the objective lens 21, and then forms an image on a pupil of the examinee's eye E, thereby illuminating the fundus.

The visible light emitted from the light source 12 travels along the same optical path as the infrared light and illuminates the fundus. The ring target of the focus chart 15 allows visible light to pass and hence the visible light emitted from the light source 12 uniformly illuminates the fundus.

The fundus observation and photographing optical system 20 includes the objective lens 21, a photographing diaphragm 23, a focusing lens 24, a relay lens 25, a total reflection mirror 26, a relay lens 27, a beam splitter 33, an imaging lens 28, and a two-dimensional image pickup element 29. The diaphragm 23 is disposed in a position conjugated with the pupil of the eye E through the objective lens 21. The two-dimensional image pickup element 29 has sensitivity to a range from infrared light to visible light and is in a conjugated relation to the fundus. The beam splitter 33 reflects the infrared light emitted from the light source 11 (and infrared light sources 35a and 35b of the anterior segment illumination optical system 30 mentioned later) while allowing visible light from the target presenting optical system 40 mentioned later to pass. Accordingly, reflection light from the fundus illuminated by the light source 11 during observation of the fundus passes through the components, from the objective lens 21 to the imaging lens 28, and then is imaged by the image pickup element 29. Simultaneously, a fixation target formed of the visible light from the target presenting optical system 40 is projected on the fundus of the examinee's eye E. During photographing of the fundus, the beam splitter 33 is switched to a beam splitter not shown having the property of allowing infrared light to pass and reflecting visible light. Thus, the image of the fundus illuminated by the visible light from the light source 12 is imaged by the image pickup element 29 via the components, from the objective lens 21 to the imaging lens 28.

The anterior segment observation optical system 30 includes the light sources 35a and 35b that emit infrared light, the objective lens 21, and an anterior segment observation auxiliary lens (hereinafter, "auxiliary lens") 22, and shares the optical system consisting of the components from the perforated mirror 19 to the image pickup element 29 of the fundus observation and photographing optical system 20. The pair of infrared light sources 35a and 35b are located symmetrically with respect to a photographing optical axis L1 and project indexes of diverged light at finity at a predetermined projection angle toward a cornea of the examinee's eye E (i.e., rectangular indexes each extending in a vertical direction with respect to the eye E). This shows an alignment condition between the eye E and the photographing part 3 in the XYZ directions and also the entire anterior segment is illuminated. Herein, the light sources 35a and 35b are rectangular LEDs.

The auxiliary lens 22 is removably placed on the optical path. Specifically, for observation of the anterior segment image through the anterior segment observation optical system 30, a controller 50 controls the driving means 22a to move the auxiliary lens 22 onto the optical axis L2. This brings the anterior segment of the examinee's eye E and the image pickup element 29 into an almost conjugated relation. On the other hand, for observation of the fundus and during photographing of the fundus, the controller 50 controls the driving means 22a to move the auxiliary lens 22 out of the optical path.

The target presenting optical system 40 shares the components, from the objective lens 21 to the relay lens 27 of the fundus observation and photographing optical system 20 and further includes an imaging lens 32 and an LCD display 31. The LCD display 31 is placed in a position conjugated with the fundus and used to display various targets such as a fixation target and a target for visual field examination under control of the controller 50 mentioned later. A target displayed on the LCD display 31 passes through the imaging lens 32, the lens 27, the mirror 26, the lens 25, the focusing lens 24, and the perforated mirror 19 and then is projected onto the fundus via the objective lens 21. In this embodiment, the relay lenses 25 and 27 and the imaging lens 32 constitute a bilateral telecentric optical system. This makes it possible to uniformly project the light irradiated from the LCD display 31 onto the fundus. It is to be noted that the fixation target and the target for visual field measurement can be designed with any shapes, sizes, and luminance, by operation of the control unit 7a.

To the controller 50, there are connected the joystick 4, the XYZ driving part 6, the control unit 7a, the response button 7b, the monitor 8, each of the light sources 11, 12, 35a and 35b, the driving means 22a, the driving means 24a, the image pickup element 29, the LCD display 31, the memory 51 serving as a storage means, a speaker 52 that generates information sound for rehabilitation mentioned later, and others. The memory 51 stores in advance measurement results as well as target presenting conditions for visual field measurement (the shapes of targets, several luminance data, etc.), and others.

The controller 50 performs display control of the monitor 8 and the LCD display 31. During observation of the anterior segment, the controller 50 further detects and processes alignment indexes from an anterior segment image picked up by the image pickup element 29. During observation of the fundus, the controller 50 detects a focus condition of the fundus based on the ring target image projected on the retina and drives the driving means 24a to move the focusing lens 24 along the optical axis L2 to adjust focusing of the fundus image picked up by the image pickup element 29. The controller 50 makes various settings based on input signals received from the control unit 7a.

Operations of the ophthalmic apparatus having the above configurations will be explained below. Herein, the following explanation is given to an example of a visual function training (rehabilitation) for an examinee to see objects by using a part of a retina, this training being conducted after distribution of retinal visual function of the examinee is checked in a visual field examination.

Firstly, when the examiner selects a visual field examination mode by operation of the control unit 7a, the controller 50 switches the display on the monitor 8 to a visual field examination screen. The examinee brings his/her face close to the apparatus so that an eye to be photographed (the eye E) is placed on the photographing window 9, and the examinee peers through the apparatus. In this state, alignment of the apparatus is performed by use of the anterior segment image. The controller 50 drives the driving means 22a to move the auxiliary lens 22 onto the optical axis L2. The light sources 35a and 35b are turned on to illuminate the anterior segment of the eye E, thereby projecting the rectangular indexes on the cornea. The controller 50 further lights a cross-shaped mark at the center of the LCD display 31 (corresponding to a position on the optical axis L2, i.e., the center of a measurement axis). The light from the LCD display 31 passes through the imaging lens 32, the beam splitter 33, and the components from the relay lens 27 to the objective lens 21. A cross-shaped fixation target is thus projected onto the fundus.

When the fixation target is projected onto the fundus, the examinee attempts to look at the fixation target carefully and thus moves an eyeball, bringing the macular area to the center of fixation. A normal macular area is superior in visual function. However, if a macular disorder is present (if no visual function is present), an examinee cannot clearly see or can only faintly see a fixation target even when he/she moves the eyeball to bring the macular area to the center of fixation.

Figure 3:
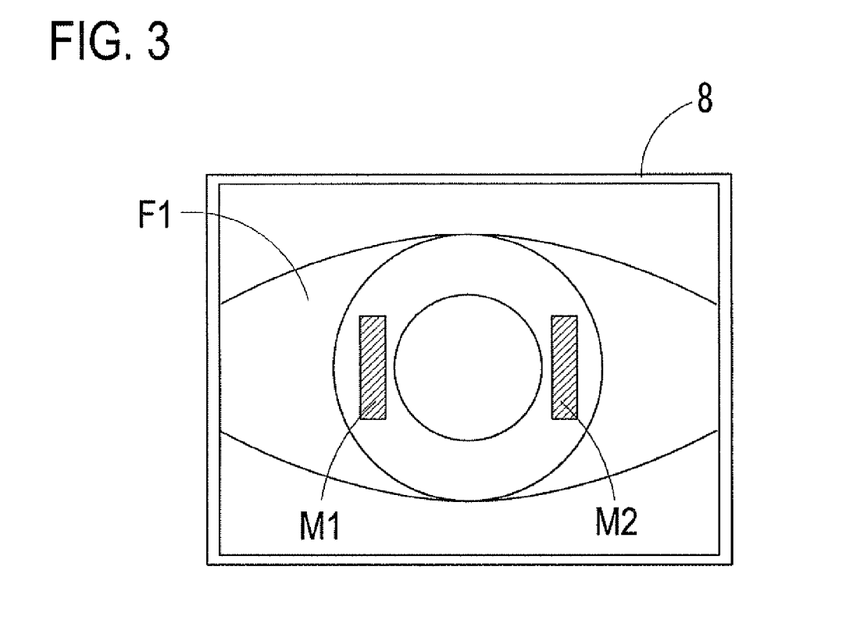
FIG. 3 is a diagram showing an example of an anterior segment image displayed on a monitor.

Herein, FIG. 3 shows an example of an anterior segment image displayed on the monitor 8. On the monitor 8, rectangular alignment indexes M1 and M2 appear on the anterior segment image F1 imaged by the image pickup element 29. The controller 50 makes alignment of the photographing part 3 with the examinee's eye E based on a received result of the alignment indexes M1 and M2. The controller 50 drives the driving part 6 to move the entire photographing part 3 in the up, down, right, and left (XY) directions for alignment so that an intermediate position in a distance between index images (alignment indexes) M1 and M2 formed by the light from the light sources 35a and 35b coincides with the center of the pupil determined from the anterior segment image. Further, the controller 50 drives the driving part 6 to move the entire photographing part 3 in the back and forth (Z) directions relative to the eye E for alignment so that an interval between the alignment indexes M1 and M2 is a predetermined interval (a predetermined value). For the details of the alignment operation, refer to WO2008/062527.

When the alignment states in the XYZ directions come to respective predetermined allowable ranges, the controller 50 judges that the alignment is completed and then starts focusing of the fundus. Specifically, the controller 50 turns off the light sources 35a and 35b and drives the driving means 22a to move the auxiliary lens 22 out of the optical path and turns on the light source 11. The controller 50 further electronically creates and displays a cross-shaped fixation target in a position on the monitor 8 corresponding to a fixation-target appearing position on the LCD display 31.

Figure 4:
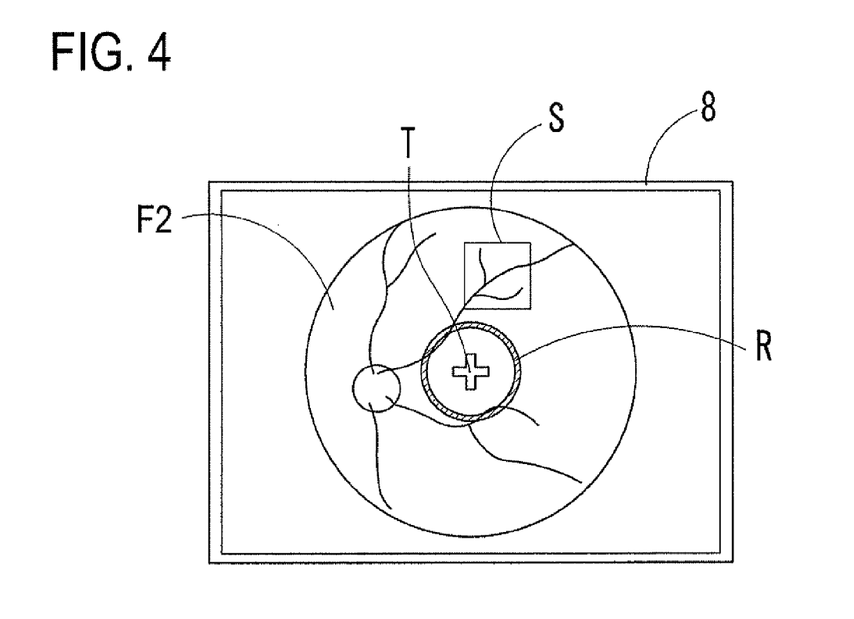
FIG. 4 is a diagram showing an example of a fundus image displayed on the monitor.

When reflection light from the fundus of the eye E illuminated by the infrared light is received by the image pickup element 29, the fundus image is displayed on the monitor 8. FIG. 4 shows an example of the fundus image displayed on the monitor 8. On the monitor 8, there appear a ring target R projected onto the fundus by the focus chart 15, the fundus image F2, and the fixation target T.

Based on the received result of the ring index R, the controller 50 controls the driving means 24a to move the focusing lens 24 so that a ring width of the ring index R becomes narrowest (the ring index R comes into focus). When the controller 50 detects that the focus state is appropriate, focus adjustment is completed.

When the fundus image F2 clearly appears on the monitor 8, the examiner makes the settings for tracking to compensate displacement or deviation of the presenting position of the target on the fundus, the displacement being likely to occur during measurement of the visual field. The displacement of the presenting position of the target is caused due to rotation of the examinee's eye E and other reasons. While observing the fundus image F2 on the monitor 8, the examiner designates a distinctive point (or region) on the fundus by operation of the control unit 7a. As the distinctive point, a distinguishable area of the fundus image such as blood vessels appearing on the fundus image is selected. Based on an input signal from the control unit 7a, the controller 50 stores, in the memory 51, the coordinate (the coordinate in the XYZ directions) of the distinctive point and a reference area S defined by a predetermined range centered on the distinctive point. Further, a frame representing the reference area S is displayed on the monitor 8. The controller 50 obtains information such as the shape of the distinctive portion and a distribution of luminance by image processing of the reference area S (distinction information to determine the distinctive portion by image processing) and stores the information in the memory 51.

The controller 50 extracts, from the received signal of the image pickup element 29, the information coinciding with the information of the reference area S stored in the memory 51, and thereby detects an amount of movement of the distinctive point (the reference area S) on the monitor 8. Therefore, by pursuing the motion (movement) of the eye found in the above way, the presenting position of the target (the examination target) on the fundus is compensated to coincide with a selected position on the monitor 8. Accordingly, even if the eye is rotated during an examination, the visual function of each area of the fundus is correctly recorded.

Subsequently, in accordance with a visual field measuring program stored in the memory 51, the controller 50 changes the luminance at a predetermined position of the LCD display 31 corresponding to each measurement point on the fundus of the examinee's eye E and presents the examination target (not shown) to the eye E. In this embodiment, the controller 50 drives pixels of the LCD display 31 so that the examination target of a predetermined brightness (luminance) level is presented at predetermined steps (e.g., at 1 dB step).

Based on the visual field measuring program, the controller 50 randomly switches the presenting position of the target on the LCD display 31 and changes the luminance. While keeping the fixation state, the examinee pushes the response button 7b when he/she recognizes the presented target. Based on the input signal, the controller 50 stores the luminance of the presented target in the memory 51 as response information on the sensitivity recognizable by the examinee at that measurement point. In the absence of a response of the examinee with the response button 7b, on the other hand, the luminance of the presented target is stored in the memory 51 as response information on the sensitivity unrecognizable by the examinee at that measurement point.

In this embodiment, the examination target is sequentially presented in predetermined positions on the LCD display 31 based on the visual field measuring program. As an alternative, an examiner may move a cursor (not shown) appearing on the monitor 8 by operation of the control unit 7a and click any position on the fundus image, thereby driving the selected portion of the LCD display 31 to present the examination target.

Figure 5:
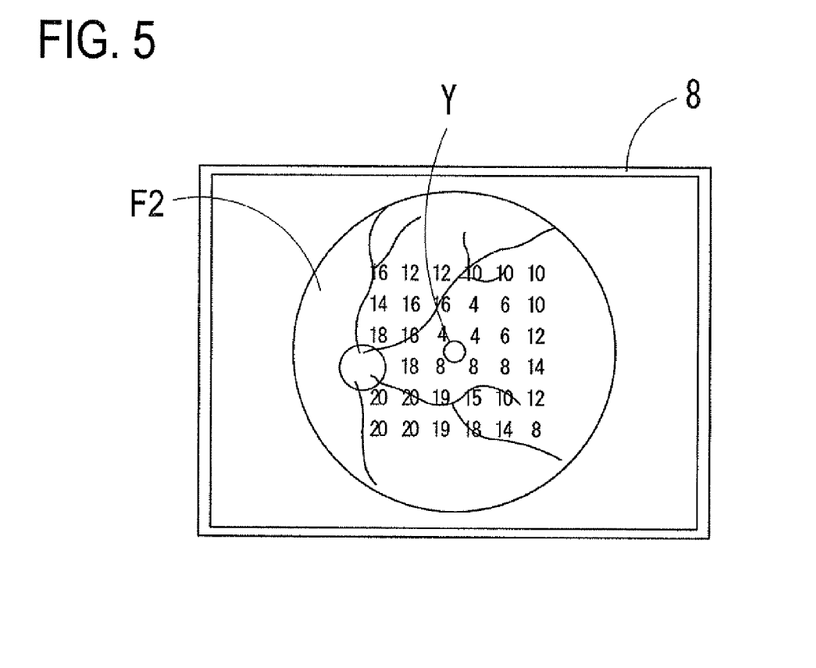
FIG. 5 is an explanatory view showing a distribution of retinal sensitivity.

After the sensitivity is measured at all the measurement points, the controller 50 causes the monitor 8 to display a distribution of the sensitivity at all the measurement points. FIG. 5 is a schematic diagram showing the distribution of retinal sensitivity displayed on the monitor 8. Herein, an attenuation value of the luminance of each presented target is used for displaying the sensitivity distribution. That is, the sensitivity distribution is displayed based on a difference from the highest luminance of each presented target. Accordingly, it is judged that a larger numeral on the monitor 8 represents a higher sensitivity in that area. In FIG. 5, a sensitivity distribution around the macular area Y is lowest. This case is judged as having a disease around the macular area Y of the examinee's eye E. On the other hand, the examiner checks which area of the fundus of the eye E is most superior in vision (has a visual function) based on a result of the visual field examination mentioned above.

Next, rehabilitation is conducted to see objects by using another area of the fundus having a visual function, instead of a diseased front surface (the macular area Y), as Preferred Retinal Locus (PRL) which is a substitute of the macular area. The controller 50 causes the monitor 8 to display a rehabilitation screen based on an input signal received from the control unit 7a operated. The examiner then determines a designated position of the PRL from the result of the visual field examination. Herein, a lower left position to the macular area Y on the monitor 8 is selected. The designated position of the PRL may be automatically determined by the controller 50 based on the sensitivity distribution.

Figure 6:
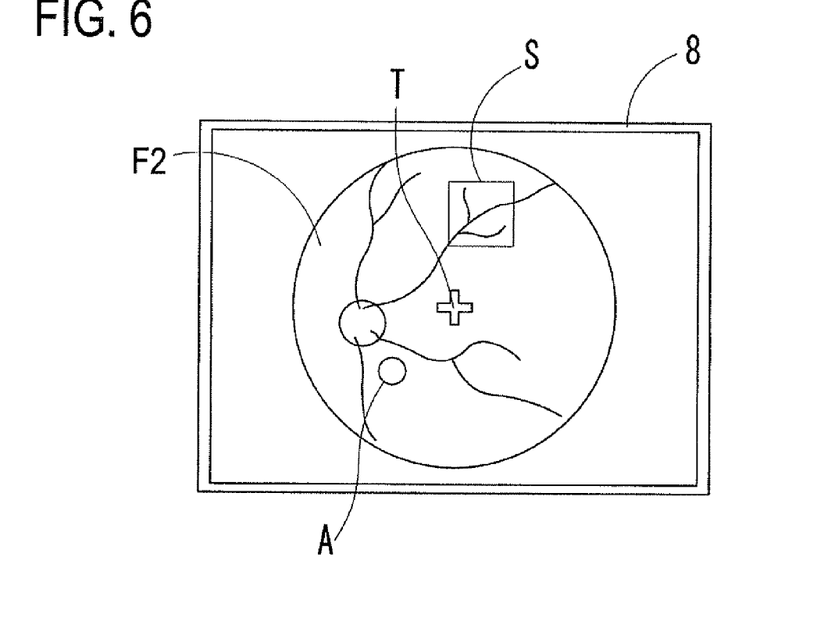
FIG. 6 is a diagram showing an example of a rehabilitation screen.

FIG. 6 shows an example of the rehabilitation screen. The examiner makes alignment between the photographing part 3 and the fundus in the same procedures as in the visual field examination while the examinee's eye E faces front (gazes at the fixation target if possible). The examiner sets the reference area S in the distinctive portion on the fundus image by operation of the control unit 7a. The reference area S may be set by automatic image processing that extracts a distinctive portion (a distinctive point) such as a papillary area and blood vessels which are high in luminance from the fundus image picked up by the image pickup element 29.

By operation of the control unit 7a by the examiner, a targeted position to be used as the PRL (an area of the fundus that will be used most frequently for vision in the future) on the fundus image displayed on the monitor 8. Herein, based on the result of the visual field examination, the area of the fundus in a lower left position to the macular area on the monitor 8 is selected (designated) as the targeted position. The controller 50 stores initial information in the memory 51 about the information on positional relationship between the coordinate of the input targeted position (the coordinate on the monitor 8) and the reference area S. As shown in FIG. 6, an index A (herein, a circle) is displayed to show the selected targeted position on the monitor 8 to the examiner.

After completion of the above settings, the examiner induces the examinee to move his/her visual line so that the index A comes close to the fixation target T displayed in the center of the LCD display 31. By changing the direction of visual line, the macular area located in the projected position of the fixation target T is gradually displaced. The controller 50 finds the amount of movement from the initial visual line position by image processing of the amount of movement of the reference area S by continuously tracking the reference area S set as the distinctive point. Based on an obtained detection result (the amount of movement), the index A on the monitor 8 is changed successively. This enables confirmation of an approaching state that the set targeted position (the area of the fundus) comes close to the fixation target T formed on the monitor 8.

The controller 50 further detects an approaching state of the fixation target T and the set index A based on the amount of movement of the reference area S. When it is detected that the index A falls within a predetermined range close to the fixation target T, the controller 50 causes the speaker 52 to generate an information sound at constant intervals. The "predetermined range" may be any range such that the visual sensitivity of that area of the fundus is obtained even when the designated fundus area does not coincide with the projected position of the fixation target T. The information on such predetermined range (size) is stored in the memory 51 in advance. The controller 50 shortens the time intervals at which the information sound is generated or gradually increases the volume of information sound to inform of the approaching of the index A to the fixation target T. This makes it possible for the examinee to easily recognize the approaching of the index A to the fixation target T.

Figure 7A:
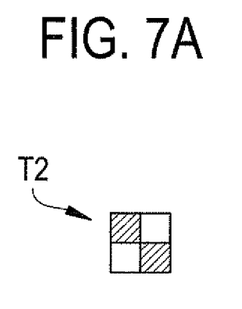
FIG. 7A is a diagram showing an example of an index to be displayed on an LCD when a targeted position and a fixation target are coincident.

When the index A comes to substantial coincidence with the position of the fixation target T (the index A is detected as entering in the predetermined range with respect to the fixation target T), the controller 50 continuously generates the information sound for a predetermined time and also switches the shape of the fixation target T by controlling the driving of the LCD 31. In this embodiment, the fixation target T presented in the form of a cross shape to the examinee's eye E is changed to an index T2 of a checkered flag pattern consisting of white and black areas alternately arranged as shown in FIG. 7A. This enables the examinee to recognize, not only by sound but also visually, the coincidence of the targeted position (the index A) and the fixation target (the fixation target T). Since more stimuli are given to the examinee, he/she can efficiently realize a new view.

As an alternative, the white and black areas of the index T2 may be alternately blinked (flicker stimulation). This configuration can not only clarify the coincidence of the targeted position and the fixation target but also give more stimuli to the retina of the examinee when the targeted position and the fixation target come to the coincidence. Thus, it is expected to improve the sensitivity of the retina.

Figure 7B:
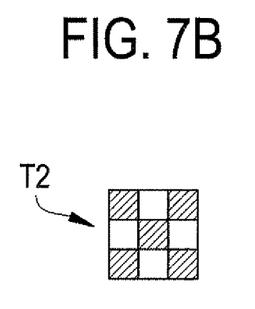
FIG. 7B is a diagram showing an example of another index to be displayed on the LCD when a targeted position and a fixation target are coincident.

The size of the index T2 may be changed arbitrarily. For instance, as shown in FIG. 7B, the index T2 may be displayed in an enlarged form when the targeted portion and the fixation target come to the coincidence state. Accordingly, this coincidence state is more clearly presented to the examinee. Besides, the LCD display 31 may be configured to switch the fixation target to indexes of various shapes to thereby make it easy for the examinee to recognize the coincidence state of the targeted position and the fixation target.

In this embodiment, the information (the coordinate) of the reference area S and the index A (a relative coordinate) are stored in association with ID information of the examinee in the memory 51. Consequently, when the examinee is subjected to a reexamination (a feedback test) at a later date, the information of the reference area as well as the information of the examinee can be called up or retrieved so that the rehabilitation is repeatedly conducted under the same conditions as in the previous time.

Associating the reference area S with the index A is performed by use of the positional information of the designated fundus area relative to the distinctive point. For instance, in an initial examination, the direction and the distance of the position (the coordinate) of the reference area S relative to the index A (the targeted position) are stored as the positional information in the memory 51. In this case, in a reexamination, the controller 50 determines the position of the index A based on the information of the position (the coordinate) of the reference area S stored in the memory 51. In this embodiment, associating of the reference area S and the index A is performed by use of direction and distance. However, the present invention is not limited thereto but may be configured such that for example the coordinate of the reference area S and the coordinate of the index A are stored as the positional information in the memory 51.

The present invention may be embodied in other specific forms without departing from the essential characteristics thereof. For instance, the above embodiment explains that a single fundus perimeter for use in both the fundus photographing and observation of an examinee's eye and the visual field examination is used to perform rehabilitation. As an alternative, the rehabilitation may be performed with a fundus camera by utilizing a visual function examination using a perimeter. Besides, the rehabilitation may be conducted on a personal computer (PC) by taking in a fundus image photographed by a fundus camera or the like via a LAN cable and others.

Specifically, the rehabilitation according to the invention can be performed by use of an ophthalmic apparatus including the fundus observation optical system for observing the fundus, the target presenting optical system for presenting a fixation lamp to an examinee's eye, the monitor for displaying a fundus image photographed by the fundus observation system, and the controller for carrying out predetermined image processing.

The invention claimed is:

1. An ophthalmic apparatus comprising:
    a fundus observation optical system including an image pickup element to observe a fundus of an examinee's eye, the fundus observation optical system being configured to obtain a fundus image of the eye;
    a target presenting optical system for presenting a fixation target and an examination target to the eye;
    a designating part for designating an area of the fundus having a visual function other than a macular area from the fundus image displayed on a monitor;
    a setting part for setting a distinctive portion of the fundus other than the designated fundus area from the fundus image displayed on the monitor, and associating a positional relationship between the set distinctive portion of the fundus with the fundus area designated by the designating part;
    a judging part for detecting an approaching state of the designated fundus area designated by the designating part and the fixation target based on the distinctive portion of the fundus set by the setting part and the presented fixation target and the associated positional relationship, and judging whether the fundus area and the fixation target are coincident in a predetermined allowable range; and
    a display control part for changing a display state of the fixation target by fixing a presenting position of the fixation target when the judging part judges that the fundus area and the fixation target are coincident in the predetermined allowable range.

2. The ophthalmic apparatus according to claim 1, wherein the display control part forms an index on the monitor to represent a position of the fundus area and changes position of the formed index based on a detection result of the judging part.

3. The ophthalmic apparatus according to claim 2, further comprising:
    a memory for storing examinee information, information of the distinctive portion of the fundus, and positional information of the fundus area by associating the informations with each other; and
    a retrieval part for retrieving, from the memory, the examinee information, the information of the distinctive portion of the fundus and the positional information of the fundus area, wherein
    the display control part forms the index on the monitor based on the information of the distinctive portion of the fundus and the positional information of the fundus area when the retrieval part retrieves the examinee information.

4. The ophthalmic apparatus according to claim 3, wherein the judging part extracts the distinctive portion of the fundus from the fundus image displayed on the monitor.

5. The ophthalmic apparatus according to claim 4, wherein the display control part switches a shape of the fixation target to a checker flag pattern consisting of white areas and black areas alternately arranged when the fundus area and the fixation target are substantially coincident with each other.

6. The ophthalmic apparatus according to claim 5, wherein the display control part selectively blinks the white areas and the black areas of the fixation target in the checker flag pattern.

7. The ophthalmic apparatus according to claim 6, further comprising:
    a speaker to generate a sound; and
    an information control part for controlling the speaker to generate an information sound when the judging part judges that the fixation target and the fundus area are coincident within the predetermined allowable range.

8. The ophthalmic apparatus according to claim 7, wherein the information control part (1) changes a sound volume of the information sound generated from the speaker or (2) generates the sound based on a detection result of the approaching state of the fixation target and the fundus area by the judging part, and when the fixation target and the fundus area are substantially coincident with each other, the sound volume of the sound generated from the speaker is maximized or the generated sound is minimized.

\* \* \* \* \*